United States Patent [19]

Kell

[11] Patent Number: 4,965,206

[45] Date of Patent: Oct. 23, 1990

[54] DETERMINATION OF BIOMASS

[76] Inventor: Douglas B. Kell, Cwmdarren, Penbont-Rhydybeddau, Cwmsylog, Aberystwyth, Dyfed SY 23 3HB, Wales

[21] Appl. No.: 479,211

[22] Filed: Feb. 9, 1990

Related U.S. Application Data

[63] Continuation of Ser. No. 99,595, Sep. 22, 1987, abandoned.

[30] Foreign Application Priority Data

Sep. 22, 1986 [GB] United Kingdom ................ 8622747

[51] Int. Cl.$^5$ .............................................. C12M 1/34
[52] U.S. Cl. ........................................ 435/291; 435/3;
435/39; 435/289; 324/663
[58] Field of Search ..................... 436/149, 150; 435/3,
435/34, 39, 4, 29, 173, 289, 291, 313, 286;
324/61 R

[56] References Cited

U.S. PATENT DOCUMENTS

| | | | |
|---|---|---|---|
| 3,339,412 | 9/1967 | Maltby | 324/61 R |
| 4,156,180 | 5/1979 | Annen et al. | 435/291 |
| 4,214,203 | 7/1980 | Coster et al. | 324/425 |
| 4,246,534 | 1/1981 | Jacobi et al. | 324/61 R |
| 4,288,741 | 9/1981 | Dechene et al. | 324/61 R |
| 4,318,992 | 3/1982 | Mila-de-la-Roca et al. | 435/291 |
| 4,547,735 | 10/1985 | Kiesewetter et al. | 324/450 |
| 4,564,944 | 1/1986 | Hiraok et al. | 435/291 |

FOREIGN PATENT DOCUMENTS

1561431 2/1980 United Kingdom.
2029026 3/1980 United Kingdom.
2131954 6/1984 United Kingdom.

OTHER PUBLICATIONS

Pethig, "Biological Membranes and Tissue", 1979, pp. 207-243.

Schwan, "Electrical Properties of Tissues and Cells", 1957, pp. 161-173, vol. 5.

"Determination of biomass concentration by capacitance measurement", by Gencer et al., Biotech. and Bioeng., vol. XXI, pp. 1097-1103 (1979).

Harris, C. M. et al., "Dielectric Permittivity of Microbial suspensions at radio frequencies: A novel method for the real-time estimation of microbiol biomass," Enzyme Microb. Technol., 1987, vol 9, Mar.

Pirt, "Principles of Microbe and Cell Cultivation," Blackwell, 1975, pp. 14-21.

Carleysmith, S. W. et al., "Fermenter Instrumentation and Control," Advances In Biotechnological Processes 3, 1984, pp. 22-23.

Meyer, H. P. et al., "Growth Control In Microbial Cultures," Ann. Rev. Microbiol., 1985, pp. 299-309.

Harris, C. M. et al., "Dielectric Permittivity of Microbial Suspensions At Radio Frequencies: A Novel Method For The Real-Time Estimation Of Microbial Biomass," Enzyme Microb. Technol., 1987, vol 9, Mar.

Pethig, R. et al., "The Passive Electrical Properties Of Biological Systems: Their Significance In Physiology, Biophysics And Biotechnology," Phys. Med. Biol., 1987, vol. 32, No. 8, 933-970, printed in the U.K.

"Biosensors Fundamentals And Applications," edited by Turner, A. P. F. et al., published by Oxford University Press, 1987, pp. 437-444.

Primary Examiner—Noah P. Kamen
Attorney, Agent, or Firm—Cushman, Darby & Cushman

[57] ABSTRACT

Method and apparatus for the determination of biomass in a suspension, such as a culture, in 'real' time and a fermentation process using the method. In the method the electrical capacitance of the suspension is measured and from the measurement the volume fraction of the suspension enclosed by the cytoplasmic membranes of the cells (biovolume) is determined.

6 Claims, 2 Drawing Sheets

DETERMINATION OF BIOMASS

This is a continuation of application Ser. No. 07/099,595, filed Sept. 22, 1987, which was abandoned upon the filing hereof.

BACKGROUND OF THE INVENTION

This invention relates to a method for the determination of biomass in a medium, to a fermentation process in which the method is used as a control feature, and to apparatus for carrying out both the method and the process.

There is increasing interest in biotechnology, both in the traditional fermentation industry and in the exploitation of living cells in new processes to produce commercially useful products such as antibiotics, vitamins, amino acids and a variety of biologically active proteins.

The productivity of fermentation processes is dependent to a considerable extend upon culture conditions. It is therefore desirable, and has now become conventional, to control those variable such as pH and dissolved oxygen tension for which sensors are available.

One of the most important variables in a fermentation process is the reactor biomass concentration, i.e. the concentration of microbial or other cells in the fermenter, since the productivity under a given set of process conditions is directly proportional to this. However, to date no accurate means has been developed for measuring the biomass content of a culture in real time, i.e. for measuring the present biomass content rather than the biomass content some time in the past.

The lack of suitable means to measure this important process variable has been commented upon by several writers in recent years, see for example: Pirt, "Principles of Microbe and Cell Cultivation", Blackwell, 1975, p 16; Carleysmith and Fox, "Fermenter Instrumentation and Control," Adv. Biotechnol. Processes 3, 1–51, 1984; and Harris and Kell, "The estimation of Microbial Biomass," Biosensors J.1, 17–84 (1985).

This last reference notes (1) that the most appropriate measure suitable for estimating biomass in real time is the biovolume, i.e. the volume fraction of a culture enclosed by the cytoplasmic membranes of the microbial or other cells within it, (2) that the only means by which biomass might be estimated in real time will be by physical as opposed to chemical measurements, and (3) that all presently available physical methods such as light scattering) for estimating biomass, are essentially unusable under the difficult conditions existing in a fermenter.

It is an object of the present invention to provide a measurement of the microbial or other biomass in fermenters in real time and preferably in situ.

SUMMARY OF THE INVENTION

According to the present invention, we provide a method for the determination of biomass in a medium comprising a suspending fluid particularly a liquid and cells, the method comprising generating a signal dependent on the electrical capacitance, at a suitable frequency, between electrodes mutally spaced in the medium, and determining from the capacitance dependent signal, the volume fraction of the medium enclosed by the cytoplasmic membranes of the cells (biovolume).

Further in accordance with the invention, we also provide a fermentation process utilising a culture comprising a suspending liquid and cells, the method comprising generating a signal dependent on the electrical capacitance, at a predetermined frequency, between electrodes mutally spaced in the culture or a sample thereof, and providing an indication if the capacitance dependent signal differs from a predetermined value or falls outside a predetermined range, and/or altering the value of a process parameter to return the signal towards the predetermined value or the predetermined range, said predetermined frequency being such that the capacitance between the electrodes depends on the volume fraction of the culture enclosed by the cytoplasmic membranes of the cells.

Yet further in accordance with the invention we provide apparatus for performing a fermentation process utilising a culture comprising a suspending liquid and cells, the apparatus comprising: a fermenter for containing the culture, electrodes mutually spaced in the fermenter so as to be in contact with the culture in use; and means for generating a signal dependent on the capacitance between the electrodes, at a predetermined frequency.

DETAILED DESCRIPTION OF THE INVENTION

The method of the invention may be used to determine biomass in any medium. The method is most useful for determining biomass in a culture and will generally be described in relation to such use in this specification. However it may also be used to determine biomass suspended in aqueous and in other suspensions and for instance in emulsions.

The apparatus may include means to determine whether the capacitance dependent signal differs from a predetermined value or falls outside a predetermined range of values.

The apparatus may further include means responsive to the means to determine, for altering one or more parameters of the process to return the capacitance dependent signal towards the predetermined value or the predetermined range.

There is an important relationship between the apparent relative permittivity of a suspension of spherical cells measured at a particular frequency, the cell radius, and the cell volume. The relationship can be expressed by the equation:

$$\epsilon_L = \frac{9\, PrC_m}{4\, \epsilon_r} + \epsilon_\infty$$

where
- $\epsilon_L$ is the apparent relative permittivity of the culture
- $P$ is the volume fraction of the culture occupied by cells
- $r$ is the cell radius
- $C_m$ is the capacitance of the cell membrane per unit area, and
- $\epsilon_\infty$ is the permittivity of the culture at a frequency which is high with respect to the measuring frequency
- $\epsilon_r$ is the permittivity of free space, approximately $8.85 \times 10^{-12}$ F/m.

For non-spherical cells, the factor 9/4 is modified.

Permittivity is related to capacitance, which can be measured, by a factor, referred to as the cell constant, which depends on the electrode number, size and geometry. The permittivity of a sample can thus be determined by measuring the capacitance between electrodes mutually spaced therein. Formerly permittivity was known as dielectric constant.

The relative permittivity of an aqueous solution is dimensionless and depends slightly on the temperature and electrical conductivity of the sample but is always in the range 60 to 85, very often being approximately 78. The permittivity of aqueous solutions, when measured at low voltages, is independent of frequency up to approximately 1 GHz, and under the conditions normally pertaining in a fermenter, is essentially unaffected by the presence of dissolved gases and non-cellular particulates matter.

The permittivity of an aqueous solution forms a reference or baseline against which the cell content of a culture may be determined.

The permittivity of a cellular suspension is strongly dependent upon frequency. For example, the permittivity at 100 kHz, of a suspension of bacterial cells of radius 0.5 $\mu$m and occupying a volume fraction of 0.1, might be approximately 250. This value will decrease towards a baseline value corresponding essentially to that of the suspending liquid as the frequency is increased.

The frequency dependent increase in permittivity found for cell suspensions over the baseline value for an aqueous solution, is known as a dispersion. Three major dispersions ($\alpha$, $\beta$, and $\gamma$ dispersions) are generally recognised, with the $\beta$-dispersion being particularly important for the invention. The $\alpha$-dispersion occurs at lower frequencies than the $\beta$-dispersion and is mainly caused by the presence of mobile ions at the cell surface. The $\gamma$-dispersion occurs at higher frequencies than the $\beta$-dispersion and is caused predominantly by the rotation of dipolar species such as water. The $\alpha$-dispersion is highly dependent on the structure of the cell wall, whilst the $\gamma$-dispersion is not specific for intact cells.

The $\beta$-dispersion of the dielectric permittivity was named by H. P. Schwan (Advances in Biological and Medical Physics, Wol. 5, 147-209, 1957). It is caused mainly by the presence of relatively ion-impermiable cellular membranes and has the approximate shape of an inverted sigmoid. Its magnitude for spherical cells, given $C_m$, can be taken to be dependent only upon cell radius and the volume fraction occupied by the cells. Other influences are, or can be taken to be, constants. Its position on the frequency axis depends upon the cell radius and the internal and external electrical conductivities. The large magnitude of the $\beta$-dispersion is due to cells having a conducting interior separated from the exterior by a poorly-conducting membrane providing a large capacitance, for example 1 $\mu$F/cm$^2$. Its magnitude is therefore directly proportional to the volume fraction occupied by the cells. The magnitude of the $\beta$-dispersion is large relative to the effects of non-cellular particles, dissolved gasses or oil droplets in the suspension. This allows the biovolume (related to the biomass by the density of the cell cytoplasm) to be measured without being significantly affected by particles or oil droplets in cell suspensions. The $\beta$-dispersion is a property of intact cells (see Pethig "Dielectric and Electronic Properties of Biological materials", Wiley, 1979) and its magnitude is directly proportional to the volume fraction of cells in a suspension up to very high volume fractions.

Suitable frequencies for measurement of biomass include frequencies at which the $\beta$-dispersion is substantially complete but at which the $\alpha$-dispersion is substantially insignificant. Measurements of the whole of the $\beta$-dispersion may be made, but optimum measuring frequencies are in the half of the $\beta$-dispersion which occurs at lower frequencies before the $\alpha$-dispersion is reached. Suitable frequencies include radio frequencies from 0.1 to 10 MHz, especially 0.1 MHz to 1 MHz, with a preferred range being 0.2 to 0.3 MHz. For large cells frequencies below 0.1 MHz may be found suitable, whilst for cultures having a high electrical conductivity, frequencies in excess of 1 MHz may be found suitable.

The method of the invention can be used to determine the biomass content of a wide range of cultures, including plant, animal and microbial cell cultures, and the fermentation process can be used to produce a wide variety of products. Most usefully, however, the method of the invention is applicable to microbial cultures containing bacterial, yeast or fungal cells. Frequently the suspending liquid will be an aqueous culture medium containing nutrients suitable for the cells suspended in it, for example compounds containing carbon, phosphorus, nitrogen and other sources of essential nutrients.

The fermentation process of the invention can be carried out in any type of fermenter. Permittivity can be determined by measuring the capacitance between electrodes mutually spaced in a sample of the culture. This can be done using a bridge or other circuit. Preferably the measuring electrodes are attached to the fermenter used in the process of the invention to enable direct on-line measurements to be made. Alternatively, samples may be withdrawn from the fermenter.

DESCRIPTION OF THE DRAWINGS AND EXAMPLES

Examples of the method and process, and an embodiment of the apparatus of the invention, will now be described with reference to the accompanying drawings, in which.

Figure 4:
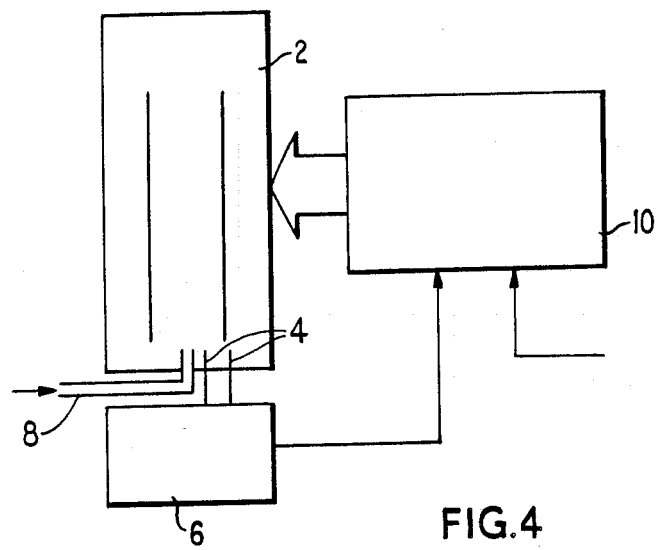
FIG. 4 is a schematic diagram of apparatus embodying the invention.

Referring to FIG. 4, a gas-lift fermenter 2 has a pair of spaced wire electrodes 4 fitted in the base. The electrodes 4 are connected to respective terminals of a Hewlett Packard low frequency impedance analyser 6 type No. 4192A. In order to reduce the effects of the capacitance inherent in the connecting leads, the impedance analyser 6 is placed as close as possible to the connections with the electrodes. Indeed, the impedance analyser may be beneath the fermenter. In order to reduce the effects of polarisation of the culture medium at the electrodes, these are platinum black. Air is supplied to the culture via an inlet 8.

Figure 1:
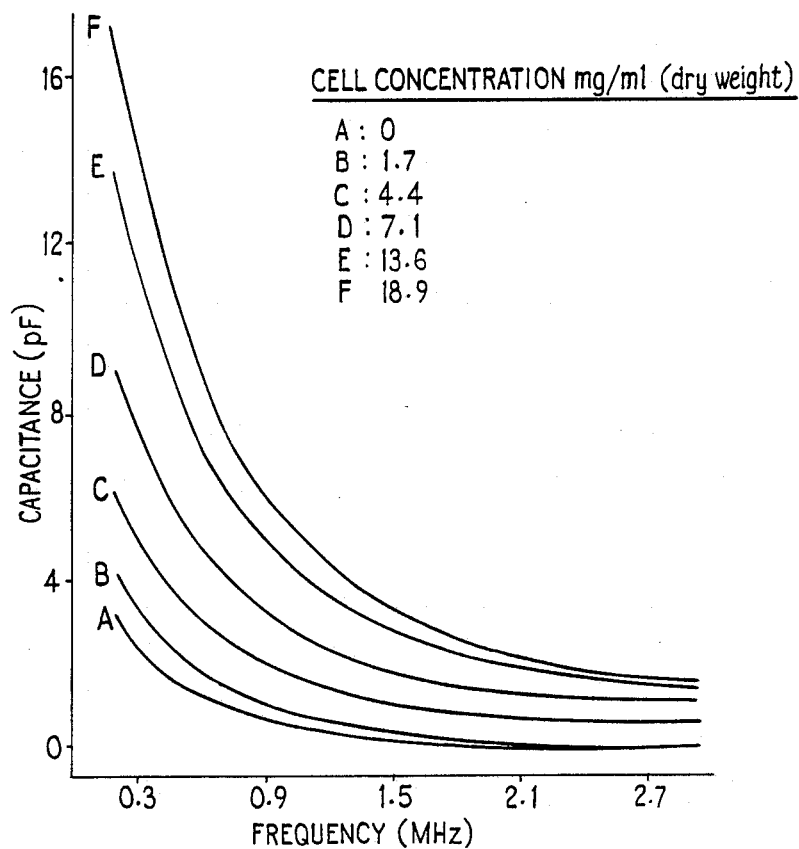
FIG. 1 shows typical variations of capacitance against frequency at different concentrations of cells in a culture.
Figure 2:
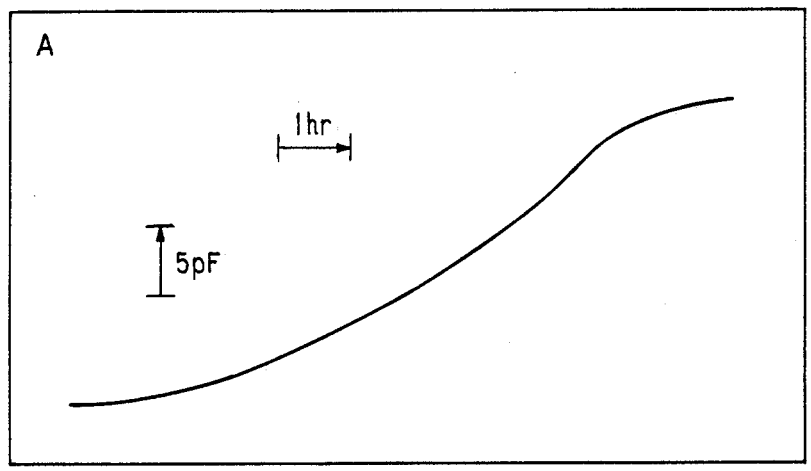
FIG. 2 shows the variation with time of capacitance, at fixed frequency, as a culture grows in a gas-lift fermenter.
Figure 3:
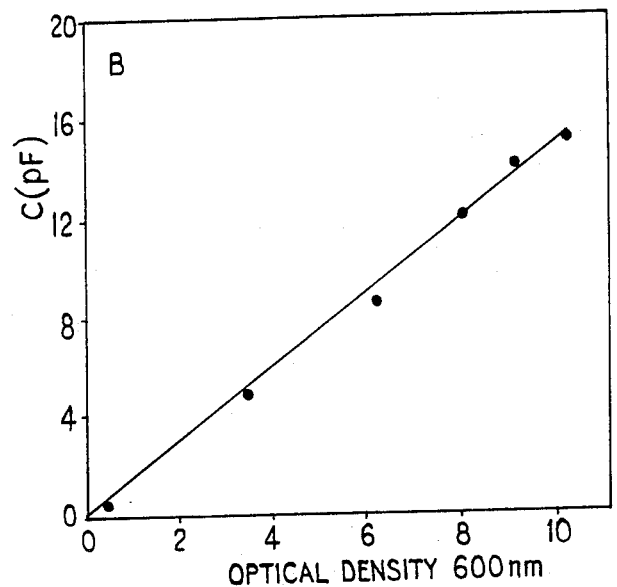
FIG. 3 shows the capacitance plotted against optical density of samples withdrawn from the fermenter.

*Saccharomyces cerevisiae* is grown in the gas-lift fermenter. The culture medium contains 5% (w/v) malt extract and 0.5% (w/v) yeast extract. The initial pH is adjusted to 4.5 and the temperature is 30 degrees centigrade. The conductance of this medium is ca. 1.57 mS/cm. Typical frequency dependent capacitance is shown in FIG. 1 at a number of different cell concentrations. It is evident that there is a sizable dielectric dispersion which depends on cell concentration. The dispersion corresponds in magnitude and relaxation time to the β-dispersion. At a fixed frequency of 0.3 MHz, FIGS. 2 and 3 show respectively, the change in capacitance with time and against the optical density of samples taken from the fermenter and appropriately diluted.

The productivity of a fermentation process is dependent on culture conditions. One of the important variables in the fermentation process which it is advantageous to measure, is the biomass concentration. It may also be advantageous to run the fermentation at a particular biomass concentration, or with the concentration within a predetermined range.

The apparatus described above can be calibrated to determine the capacitance at a fixed frequency, say 0.3 MHz, corresponding to particular biomass concentrations. The apparatus may be calibrated to indicate biomass directly.

The on line measurement of capacitance, or biomass, provides a capacitance dependent signal which is fed to a process controller 10 where it is compared with a reference signal. Alternatively the process controller may determine whether the capacitance dependent signal lies within a predetermined range. The process controller is arranged to adjust one or more parameters of the fermentation process to return the capacitance dependent signal towards the reference signal value or towards the predetermined range. Parameters which may be adjusted include the oxygen rate, i.e. The air supply rate, the dilution rate, the rate of addition of nutrients or new culture in a continuous process, the temperature, and so on.

A preferred specific embodiment of an apparatus for use in the invention is described in our co-pending UK Application No. 8622748, corresponding to U.S. Pat. No. 99,594, the contents of which are incorporated herein by reference.

I claim:

1. A method for the determination of biomass in a medium comprising a suspending fluid and cells, electrodes being mutually spaced in said medium, the method comprising the steps of:
    (a) generating a signal dependent on the dielectric permittivity of the material in the bulk of said medium, but essentially independent of the conductivity of the medium, using electrical capacitance measurement, and
    (b) determining the volume fraction of the medium enclosed by the cytoplasmic membranes of the cells from said permittivity dependent signal.

2. A fermentation process utilizing a culture comprising a suspending fluid and cells, said process comprising the steps of:
    (a) generating a signal dependent on the dielectric permittivity of the culture in the bulk of the culture using electrical capacitance measurement, at a suitable frequency, between electrodes mutually spaced in said culture or a sample thereof;
    (b) providing an indication if the permittivity dependent signal differs from a predetermined value or falls outside a predetermined range, and/or
    (c) altering the value of a process parameter to return said signal towards the predetermined value or range, said predetermined frequency being such that the dielectric permittivity of the material in the bulk of the culture between the electrodes depends on the volume fraction of the culture enclosed by the cytoplasmic membranes of the cells.

3. Apparatus for performing a fermentation utilizing a culture comprising a suspending liquid and cells, the apparatus comprising:
    (a) a fermenter for containing the culture;
    (b) electrodes mutually spaced in the fermenter so as to be in contact with the culture in use; and
    (c) means for generating a signal dependent on the dielectric permittivity in the bulk of the culture, using electrical capacitance measurement between the electrodes, at a predetermined frequency.

4. An apparatus as in claim 3 further comprising means for determining whether the permittivity dependent signal differs from a predetermined value or falls outside a predetermined range.

5. An apparatus as in claim 4 further comprising means for altering one or more parameters of the process to return the permittivity dependent signal towards the predetermined value or the predetermined range, responsive to said means for determining.

6. An apparatus as in claims 3, 4 or 5, wherein said predetermined frequency is in the range 0.1 MHz to 10 MHz.

* * * * *